(12) United States Patent
Mackool

(10) Patent No.: US 8,475,480 B2
(45) Date of Patent: Jul. 2, 2013

(54) MULTI-SLEEVED SURGICAL ULTRASONIC VIBRATING TOOL SUITED FOR PHACOEMULSIFICATION IN A MANNER THAT PREVENTS THERMAL INJURY TO OCULAR TISSUE

(75) Inventor: Richard James Mackool, Greenwich, CT (US)

(73) Assignee: Alcon Research Ltd, Fort Worth, TX (US)

( * ) Notice: Subject to any disclaimer, the term of this patent is extended or adjusted under 35 U.S.C. 154(b) by 313 days.

(21) Appl. No.: 12/984,008

(22) Filed: Jan. 4, 2011

(65) Prior Publication Data

US 2012/0172786 A1    Jul. 5, 2012

(51) Int. Cl.
*A61B 17/32* (2006.01)
(52) U.S. Cl.
USPC .......................................... 606/169
(58) Field of Classification Search
USPC ............ 433/81, 82, 84, 86, 102, 119; 604/19, 604/22, 35, 48, 93.01, 96.01, 272; 606/107, 606/161, 166–170
See application file for complete search history.

(56) References Cited

U.S. PATENT DOCUMENTS

| | | | |
|---|---|---|---|
| 4,869,715 A | 9/1989 | Sherburne | |
| 5,464,389 A | 11/1995 | Stahl | |
| 5,505,693 A * | 4/1996 | Mackool | 604/22 |
| 5,725,495 A | 3/1998 | Strukel et al. | |
| 5,743,871 A | 4/1998 | Strukel et al. | |
| 5,919,157 A | 7/1999 | Strukel | |
| 5,964,777 A | 10/1999 | Drucker | |
| 6,117,149 A | 9/2000 | Sorensen et al. | |
| 6,159,175 A | 12/2000 | Strukel et al. | |
| 6,238,400 B1 | 5/2001 | Bays | |
| 6,299,591 B1 | 10/2001 | Banko | |
| 6,340,355 B1 | 1/2002 | Barrett | |
| 6,428,501 B1 | 8/2002 | Reynard | |
| 6,491,709 B2 | 12/2002 | Sharma et al. | |
| D478,383 S | 8/2003 | Timm et al. | |
| 6,712,797 B1 | 3/2004 | Southern, Jr. | |
| 7,014,629 B2 | 3/2006 | Mackool | |
| 7,351,219 B2 | 4/2008 | Mackool | |
| 7,572,244 B2 * | 8/2009 | Weisel et al. | 604/27 |
| 7,762,978 B2 | 7/2010 | Mackool | |

* cited by examiner

*Primary Examiner* — Ryan Severson
*Assistant Examiner* — Ashley Fishback
(74) *Attorney, Agent, or Firm* — Hess Patent Law Firm LLC; Robert J. Hess

(57) ABSTRACT

A multi-sleeve handpiece for performing phacoemulsification with a vibratory, ported needle and for cooling an exterior of an incision. The vibratory, ported needle breaks up and aspirates broken eye tissue. The handpiece has at least one inner sleeve that guides irrigation fluid to the eye and/or reduces friction between the vibrating tool and the surrounding rigid sleeve or tissues. The handpiece has an outer, cooling sleeve that is concentric with the inner sleeve and the needle and whose distal end has peak and valley formations. The cooling sleeve is collapsible to engage incision tissue with the peak formations and allow the cooling fluid to flow across the valley formations to cool the tissue via heat transfer.

23 Claims, 6 Drawing Sheets

MULTI-SLEEVED SURGICAL ULTRASONIC VIBRATING TOOL SUITED FOR PHACOEMULSIFICATION IN A MANNER THAT PREVENTS THERMAL INJURY TO OCULAR TISSUE

BACKGROUND OF THE INVENTION

1. Field of the Invention

The invention relates to a multi-sleeved surgical ultrasonic vibrating tool to perform phacoemulsification. The sleeves channel fluid; there may be an inflexible inner sleeve that serves to reduce friction between itself and the surrounding sleeve, and thereby mitigate against thermal damage to surrounding tissues and channels irrigation fluid to cool the same, a flexible middle sleeve that channels irrigation fluid into the eye, and an outer sleeve to direct fluid to cool ocular tissue external to the incision.

2. Discussion of Related Art

According to the Eye Surgery Education Council of the American Society of Cataract and Refractive Surgery Foundation (http://www.lasikinstitute.org/Phacoemulsification.html), phacoemulsification is the most common and advanced cataract surgery technique.

"The surgeon first makes a small incision at the edge of the cornea and then creates an opening in the membrane that surrounds the cataractous lens. This thin membrane is called the capsule. Next, a small ultrasonic probe is inserted through the opening in the cornea and capsule. The probe's vibrating tip breaks up or "emulsifies" the cloudy lens into tiny fragments that are suctioned out of the capsule by an attachment on the probe tip. After the lens is completely removed, the probe is withdrawn leaving only the clear (now empty) bag-like capsule, which will act as support for the intraocular lens (IOL).

Phacoemulsification allows cataract surgery to be performed through a very small incision in the cornea. Stitches are seldom needed to close this tiny entry, which means that there is less discomfort and quicker recovery of vision than with other surgical techniques. Small incisions do not change the curvature of the cornea like larger ones that were required with older surgical techniques. This allows for more rapid rehabilitation of vision and possibly less dependence on glasses for good distance vision.

After removal of the cataract-damaged lens, an artificial intraocular lens (IOL) is implanted. Made from soft acrylic or solid medical-grade silicone, IOLs are folded so they can be implanted with a small injector, which uses the same incision through which the phaco probe was inserted at the beginning of the procedure. As the IOL is implanted, it unfolds and anchors itself behind the eye's pupil over the remaining clear capsule. The IOLs to be implanted are selected based on power calculations made before surgery."

The online Wikipedia describes the surgical technique of phacoemulsification:

"Before the phacoemulsification can be performed, one or more incisions are made in the eye to allow the introduction of surgical instruments. The surgeon then removes the anterior face of the capsule that contains the lens inside the eye. Phacoemulsification surgery involves the use of a machine with microprocessor-controlled fluid dynamics. These can be based on peristaltic or a venturi type of pump.

The phaco probe is an ultrasonic handpiece with a titanium or steel needle. The tip of the needle vibrates at ultrasonic frequency to sculpt and emulsify the cataract while the pump aspirates particles through the tip. In some techniques, a second fine steel instrument called a "chopper" is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only.

An irrigation-aspiration probe or a bimanual system is used to aspirate out the remaining peripheral cortical matter, while leaving the posterior capsule intact. As with other cataract extraction procedures, an intraocular lens implant (IOL), is placed into the remaining lens capsule. For implanting a PMMA IOL, the incision has to be enlarged. For implanting a foldable IOL, the incision does not have to be enlarged. The foldable IOL, made of silicone or acrylic of appropriate power is folded either using a holder/folder, or a proprietary insertion device provided along with the IOL.

It is then inserted and placed in the posterior chamber in the capsular bag (in-the-bag implantation). Sometimes, a sulcus implantation may be required because of posterior capsular tears or because of zonulodialysis. Because a smaller incision is required, few or no stitches are needed and the patient's recovery time is usually shorter when using a foldable IOL."

Indeed, a common method of cataract removal requires the use of a vibrating ultrasonic needle that can be inserted through a small incision in the human eye. The vibrating needle can cause temperature elevation within the incision. This temperature elevation is a problem that requires certain protective mechanisms, that is, precautions and/or technologies, in order to reduce the possibility of creating a thermal injury to the surrounding ocular tissues. Such protective mechanisms include the creation of an incision that is substantially larger than the ultrasonic needle or probe, with resultant leakage of fluid from the eye around the vibrating tip serving as a coolant. Other protective mechanisms include those previously devised by the applicant, and include the use of a rigid sleeve inserted between the vibrating needle and the soft, pliant outer sleeve through which infusion is delivered into the eye, or the use of an optical device to monitor the temperature in the vicinity of the ultrasonic needle or probe and discontinue needle or probe vibration in the event of undesirable temperature elevation.

There has been interest in performing ultrasonic removal (phacoemulsification) of human cataracts in a manner that divides the location of the entry of the infusion source and the ultrasonic needle into the eye into two smaller incisions in the eye. However, there has been concern that the use of a "bare" ultrasonic needle could increase the risk of thermal injury to the surrounding tissues because of the absence of surrounding rigid sleeves and the fluid contained within such rigid sleeve (s) that normally serve as coolants. It has therefore been advocated and it is the current practice to employ a method in which the surgical incision for insertion of the ultrasonic needle or probe be made substantially larger than that required for insertion of the needle or probe in order to permit fluid leakage from inside the eye to leak alongside the ultrasonic needle and thereby cool the latter.

While such a method will undoubtedly reduce the temperature of the needle, it is not desirable to have fluid leakage from the eye as this increases the trauma inflicted by fluid circulating through the eye during the procedure (a greater amount of fluid passes through the eye during the procedure), control of the pressure within the eye can be compromised by the leakage and this can lead to collapse of the eye, such collapse leading to contact of the vibrating ultrasonic needle with delicate ocular tissues such as the iris, cornea or lens capsule.

Based on the experience of applicant, who has performed tens of thousands of ultrasonic cataract extractions, the greatest risk of thermal injury occurs at the external surface of the incision in the eye where such surface is in contact with the vibrating ultrasonic needle. This appears to be casually related to the fact that the environmental air is a poor conductor of heat away from the eye and the external tissues are therefore more likely to retain thermal energy transferred from the ultrasonic needle.

The present inventor invented the subject matter of U.S. Pat. Nos. 7,762,978 and 7,351,219, which reveals a method and instrumentation for cooling a surgical incision. Indeed, the patented method and instrumentation for cooling the surgical incision enables a degree of cooling to the area of a surgical incision that is more rapid and efficient than air cooling to prevent a temperature rise at the incision to a medically unacceptable level during the use of a surgical device.

It is desirable to provide a degree of cooling to the area of a surgical incision that is more rapid and efficient than that of air cooling to prevent a temperature rise at the incision to a medically unacceptable level during the use of a surgical device, where the surgical device is equipped with one or more sleeves that may include a rigid sleeve that directs fluid to irrigate the eye during phacoemulsification.

SUMMARY OF THE INVENTION

One aspect of the invention resides in a surgical tool having an ultrasonically driven vibratory needle equipped with one or more sleeves: one or more inner rigid sleeves serving to guide the infusion of irrigating fluid flow into the eye and/or reduce friction between the needle and the tissue or other sleeve that surrounds the rigid sleeve, and an outer cooling sleeve serving to guide cooling fluid flow to reach an exterior surface of an eye incision. The outer cooling sleeve has a distal end shaped with peak and valley formations that allow the fluid flow to pass over the valleys and outward. The valley formations are arranged closer to the proximal end of the rigid sleeve than are the peak formations.

The outer cooling sleeve is compressible and expandable in its axial direction. The vibratory needle defines an interior chamber and terminates at a tip. All of the various sleeves are hollow and elongated between proximal and distal ends. The needle extends within confines of the sleeves and the needle tip projects outwardly beyond the distal end of the sleeves. The rigid sleeve has an interior surface and interior space through which there is a passage for irrigation fluid flow.

There is a cooling passage between the outer cooling sleeve and the inner rigid sleeve. The cooling fluid flows through the cooling passage by traveling in a direction to the distal end of the cooling sleeve and away from the proximal end of the cooling sleeve, the fluid flows across the valley formations to cool the incision via the peak formations at or near the tissue at the incision.

That is, the cooling sleeve abuts or nearly abuts an exterior or external surface of the incision of the eye without entering the interior of the incision. The cooling sleeve collapses (shortens) or expands (elongates) as the needle is repetitively advanced and partially withdrawn through the incision.

BRIEF DESCRIPTION OF THE DRAWINGS

For a better understanding of the present invention, reference is made to the following description and accompanying drawing, while the scope of the invention is set forth in the appended claims:

DESCRIPTION OF THE PREFERRED EMBODIMENT

Turning to FIGS. 1-4, the present invention is a surgical tool that includes an outer cooling sleeve 10, that may include a malleable fluid delivery sleeve within it, and that may include an inner rigid sleeve 20, and a vibratory needle 30. Preferably, the outer cooling sleeve 10 is made of a soft and plant material. The outer cooling sleeve 10 compresses/collapses or expands, such as in an accordion-like manner. The inner rigid sleeve 20 is preferably made of a rigid, inflexible material. The vibratory needle 30 has a hollow shaft and is ported at its distal end region.

The hollow shaft of the vibratory needle 30 is preferably concentric with the inner rigid sleeve 20 and the other sleeve (s). The distal tip of the vibratory needle 30 is inserted through a small incision, together with the ported end of the inner rigid sleeve 20 and/or an additional malleable sleeve that delivers fluid into the eye. To reduce the risk of thermal injury to an external tissue area at the incision, the outer cooling sleeve 10 guides cooling fluid to cool the external tissue area at the incision. In effect, a conventional phacoemulsification instrument may be used to aspirate and irrigate the eye through the same incision, perhaps 1.0 to 2.5 mm in width, except that such is equipped with the outer cooling sleeve.

The vibratory needle 30 would ordinarily be required to travel more than 1 millimeter to reach the interior of the eye from the outside the incision. The vibratory needle 30 is then driven in a conventional manner at ultrasonic speeds to vibrate or oscillate, although the needle may alternatively be driven at higher or lower speeds within the meaning of the invention.

Figure 1:
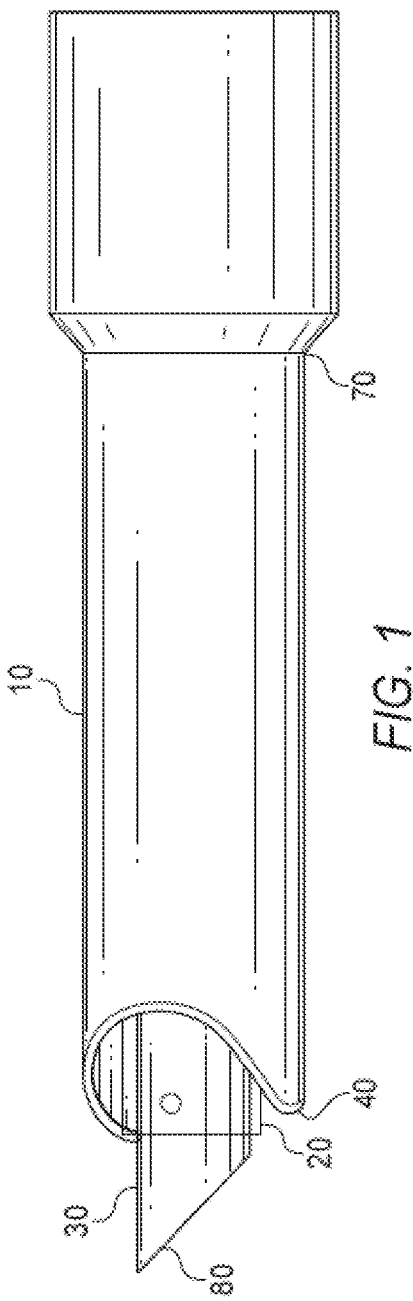
FIG. 1 is a schematic representation of an outer cooling sleeve in accordance with the invention with the distal portion of the needle partially exposed.
Figure 2:
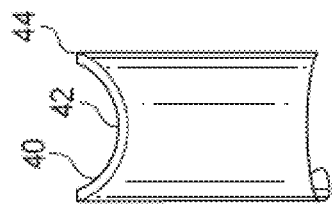
FIG. 2 is a schematic representation of one side of a distal portion of the outer cooling sleeve of FIG. 1.
Figure 3:
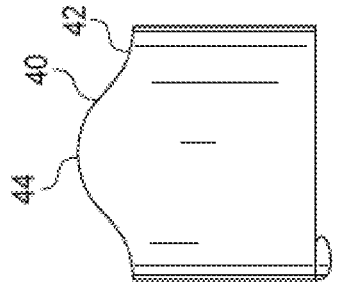
FIG. 3 is a schematic representation of a further side of the distal portion of the outer cooling sleeve that is adjacent to the side shown in FIG. 2.
Figure 4:
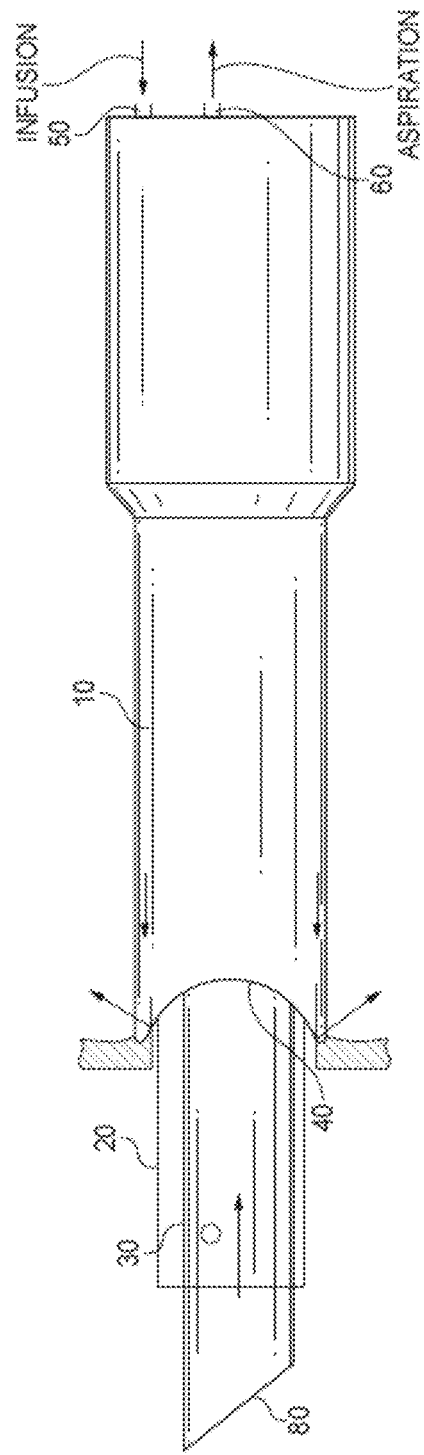
FIG. 4 is a schematic representation of fluid flows in accordance with the invention with the needle advanced and the outer cooling sleeve abutting an incision.

As shown in FIGS. 1 and 4, the outer cooling sleeve 10 is arranged to abut the external incision, but does not enter the incision. Such a cooling sleeve 10 may be made of extremely soft and pliant material so that it may compress/collapse or expand, such as in an accordion-like manner. As the needle 30 repetitively advances (FIG. 5) and partially withdraws (FIG. 1) during performance of the surgical procedure, the outer cooling sleeve 10 collapses in response to the vibratory needle 30 being advanced and lengthens in response to the vibratory needle 30 being partially withdrawn from the incision. For purposes of convenience of illustration, the portion of the distal end 40 of the cooling sleeve 10 that would normally be blocked from view by the protruding, vibratory needle 30 is depicted in FIG. 1.

The distal end 40 of the cooling sleeve 10 may be scalloped or serrated (FIGS. 1-4) so that there is no impediment to the flow of fluid along an exterior of the inner malleable or rigid sleeve 20 and (if accessible) the tip of the vibratory needle 30 and then over the external portion of the incision. Such flow will act to substantially cool the accessible part of the needle and will also reduce the transmission of thermal energy from the needle shaft and eventually to the tissue surrounding the needle. In addition, such flow will also directly cool the tissues surrounding the incision.

In order to increase the beneficial cooling effect of the fluid in any of the sleeves, the fluid may be a liquid cooled by refrigeration prior to its actual use. Indeed, the rate of cooling and efficiency of heat transfer to the fluid flow is greater than that attained from the environmental airflow.

One or more recesses are between a distal end of the cooling sleeve and an external wall of the incision in the eye for allowing fluid flow as a result of the distal end being serrated or scalloped. These recesses form the valleys of the serrations or scallops, while the peaks of the serrations or scallops abut the exterior of the incision.

The vibratory needle 30 is driven by a driver within a surgical handpiece to oscillate or vibrate at ultrasonic or subsonic speeds. The surgical handpiece has an infusion port 50 and an aspiration (suction) port 60. A suction source (vacuum) is connected to the aspiration portion to suction through the interior chamber of the needle to provide aspiration. A refrigerated cooling fluid source is connected to deliver fluid through the inner rigid sleeve 20 and the outer cooling sleeve 10.

At the distal end 40 of the outer cooling sleeve 10, the fluid flows across valley formations 42 but not across peak formations 44 that abut the exterior of the incision. The distal end 40 may have serrations or scallops that define the valley and peak formations. FIG. 4 includes flow arrows to show the direction of cooling fluid flow through a passage between the inner surface of the outer cooling sleeve 10 and the external surface of the needle 30 and across the valley formations 42 of the distal end 40. Flow arrows are also present to show the direction of aspiration flow through the internal chamber needle 30. The valley formations 42 are closer to the proximal end 70 of the rigid sleeve than are the peak formations 44. As the fluid flow travels across the valley formations 42, the exterior of the incision cools (FIG. 4). While such cooling of the incision takes place, the needle may be driven to vibrate or oscillate while the needle tip 80 is aspirating the interior of the eye through the incision. The interior chamber of the needle and thereby the tip is in fluid communication with the suction source via the suction port 60.

The vibrating or oscillating of the needle tip is responsible for generating heat, either through rubbing contact with tissue at the incision or from heat caused by operation of the driver that vibrates or oscillates the needle. The cooling of the tissue from the fluid flow traveling across the valley formations helps prevent thermal damage to the tissue from arising that would otherwise result from the heat generation.

Figure 5:
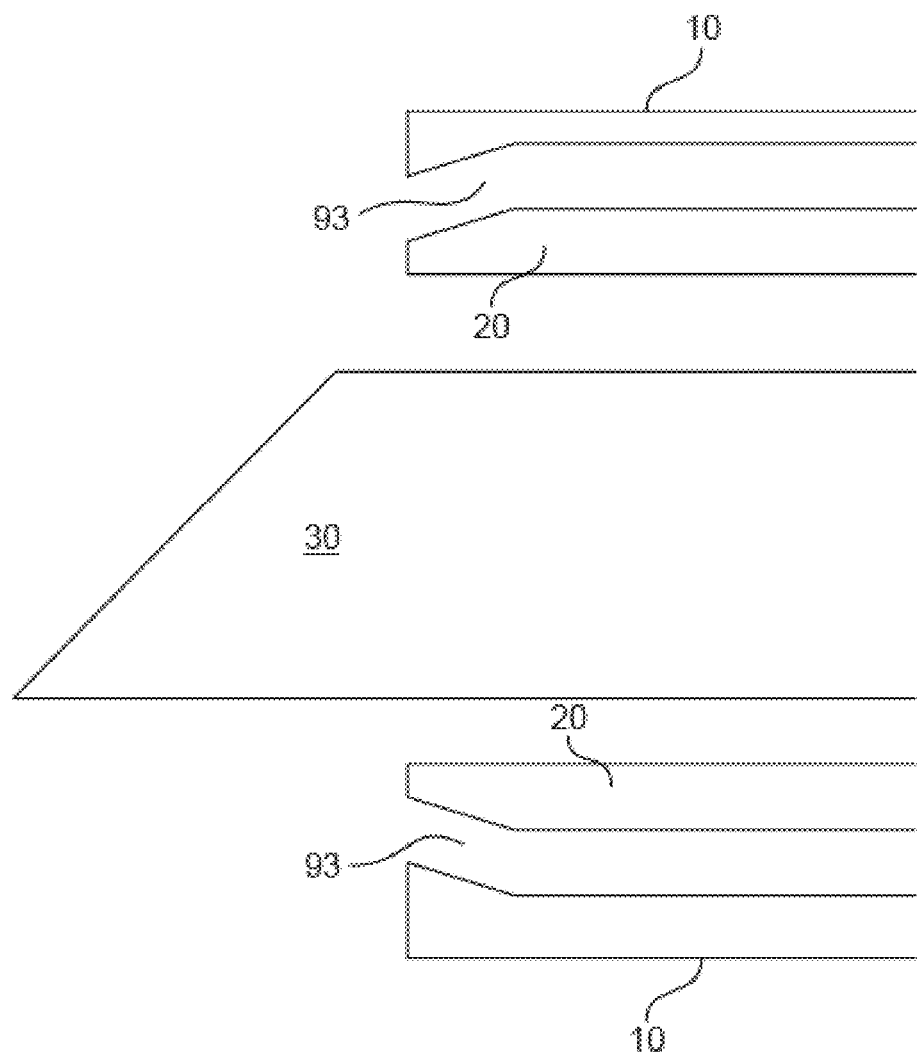
FIG. 5 is a schematic sectional representation of a further embodiment.

If desired as shown in FIG. 5, the distal ends of the outer surface of the inner rigid sleeve 20 and the inner surface of the outer cooling sleeve 10 may be inclined inwardly to channel flow inwardly toward the entrance of the incision tissue to form an inclined passage 93. Such inclined surfaces may help lessen the turbulence of the cooling fluid flow upstream of the incision by promoting laminar flow, which may provide better heat transfer. However, the inner rigid sleeve 20 needs to remain rigid, so if providing an inclined surface unduly weakens the integrity of the distal end of the inner rigid sleeve 20, then such an inclined surface should not be provided due to safety concerns if the rigid sleeve collapses on the needle 10 to prevent irrigation flow. As concerns the cooling sleeve 10, the risk of collapse onto the infusion is less harmful and, further, unlikely if its peak formations of the distal end are pressing the incision tissue.

Figure 6:
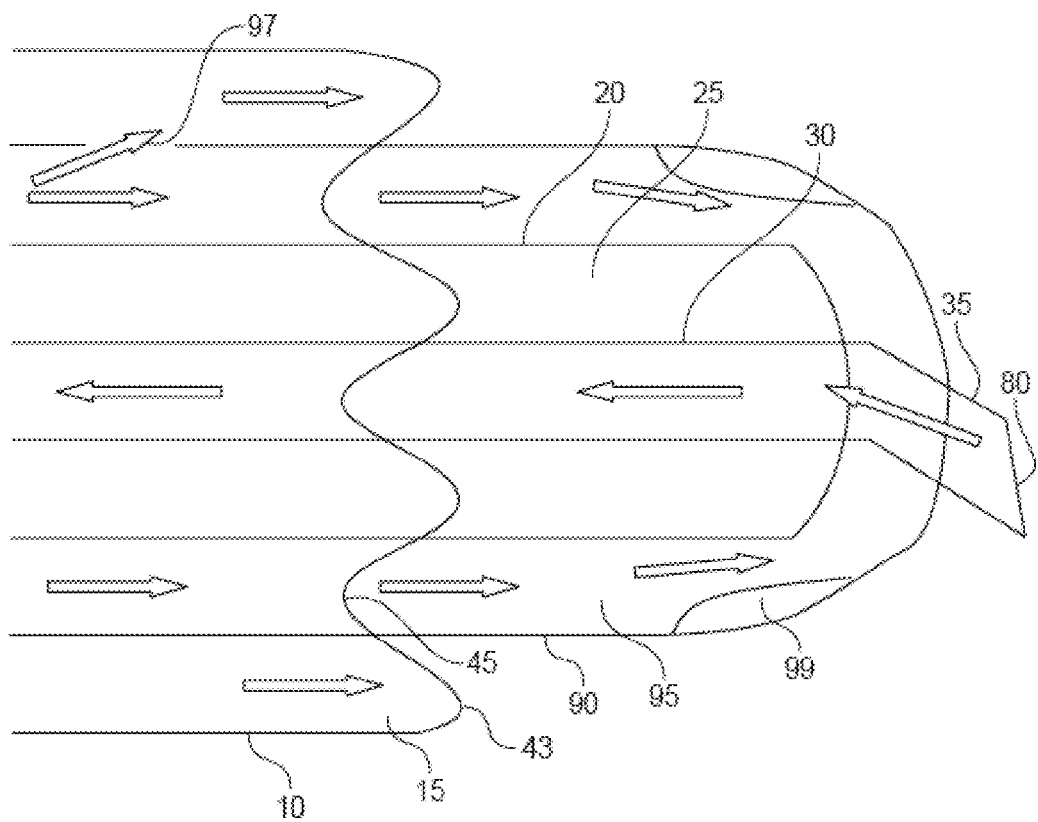
FIG. 6 is a schematic sectional representation of another embodiment.

Turning to FIG. 6, a multi-sleeved embodiment is shown that includes the inner rigid sleeve 20, a middle sleeve 90 and the outer sleeve 10. The inner rigid sleeve 20, which is inflexible, serves to reduce friction between the vibratory needle 30 and whatever surrounds the inner rigid sleeve 20, such as a soft rigid sleeve or tissue (in the absence of any other sleeve surrounding the inner rigid sleeve 20).

Indeed, only the inner rigid sleeve 20 is responsible for reducing friction. A small amount of fluid does flow beneath it on its way into the eye rather than the majority of fluid that passes external to it (and beneath the middle sleeve 90) and then into the eye. The middle sleeve 90 is responsible for delivering fluid into the eye. The outer sleeve 10 delivers fluid to the external surface of the eye at the region of the incision to cool ocular tissue external to the incision.

All the sleeves are concentric with each other and with a shaft 30 of an elongated hollow needle, whose tip 35 may be angled obliquely relative to the shaft 30. The needle is driven to vibrate, preferably at ultrasonic speeds. The oblique tip 35, because of its angulation, may produce a desirable torsional movement when vibrating at ultrasonic speeds to break up targeted tissue.

The distal end of the outer sleeve 10 may have a sinusoidal pattern of peaks 43 and valleys 45 so that when the distal end of the outer sleeve 10 is pressed against tissue about the incision of the eye, fluid may be channeled through the outer passage 15 (between the outer sleeve 10 and the middle sleeve 90) to deliver the fluid to the ocular surface by the incision and out via the valleys 45. In lieu of a sinusoidal pattern such as where the distal end of the outer sleeve 10 is flat, perforations may be provided in the outer sleeve 10 that neighbor the distal end of the outer sleeve 10 that permit fluid to exit the outer sleeve 10 via the perforations, drain downward along the exterior surface of the outer sleeve 10 to arrive at the tissue that would then be cooled by the drained fluid.

The middle sleeve 90 may have perforations 97 that permit the diversion of a portion of fluid flow from the middle passage 95 (between the middle sleeve 90 and the inner sleeve 20) to enter the outer passage 15 and a portion to continue along the middle passage 95. The perforations 97 are in alignment with confines of the outer sleeve 10 and may be along most of the length of the outer sleeve 10. That is, there is no need for perforations in the middle sleeve 90 to be near the distal end of the middle sleeve 90 to enable fluid flow to the outer passage 15 if the distal end of the middle sleeve 90 enters the incision, because the outer sleeve 10 does not enter the incision but rather abuts against ocular tissue outside the incision.

The hollow needle shaft 30 is connected to an aspiration source to aspirate cut tissue via its tip 80 and through the needle's hollow cavity of the shaft 30. The inner rigid sleeve 20 is preferably free floating in the sense that the inner rigid sleeve 20 is unattached, but its back and forth movement is confined preferably by protrusions elsewhere on the surgical handpiece. If needed, an inwardly extending protrusion 99 may be provided at the distal end of the middle sleeve 90 to channel fluid flow in an angled, inward direction (converging). The proximal ends of the middle sleeve 90 and the outer sleeve 10 are preferably secured to the surgical handpiece in a liquid-tight manner at a location upstream of the proximal end of the inner sleeve 20.

Figure 7:
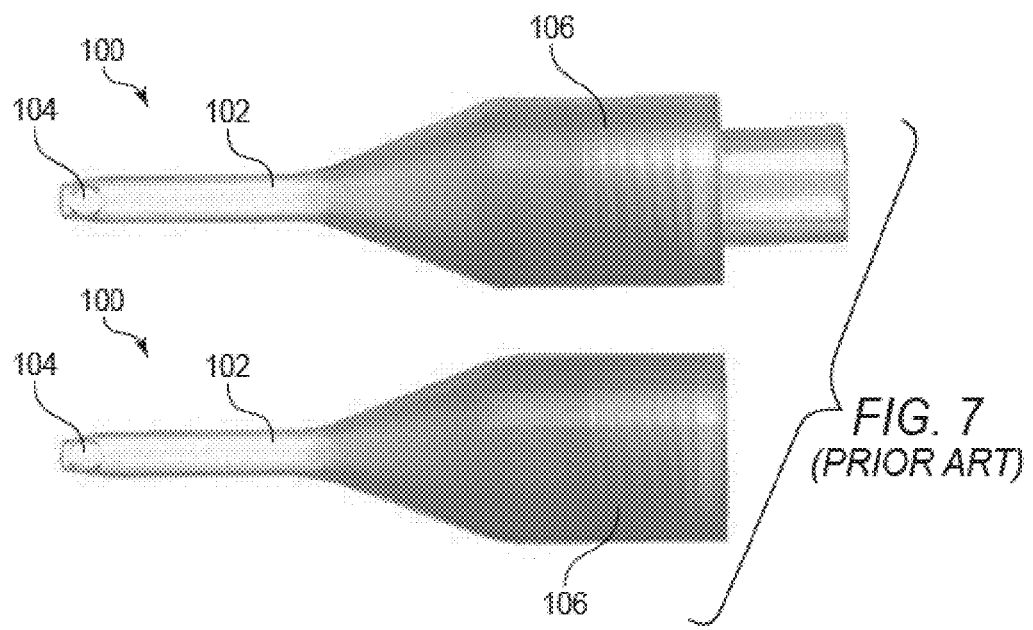
FIG. 7 is a side view of conventional tips each with a single irrigation sleeve for use with a ultrasonic, vibrating, phacoemulsification surgical handpiece.
Figure 8:
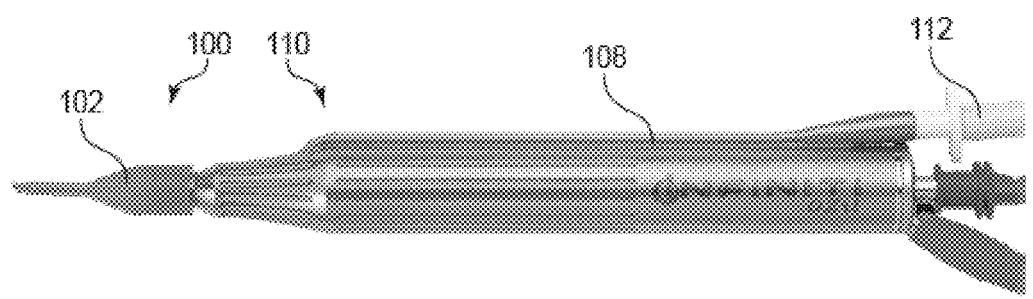
FIG. 8 is a side view of an ultrasonic, vibrating, phacoemulsification surgical handpiece secured to one of the conventional tips with the single sleeve of FIG. 7.

The manner in which fluid is delivered to the middle passage 95 may be in accordance with the manner in which irrigation fluid is delivered to a conventional passage between the needle and a sleeve, such as for ultrasonic vibratory phacoemulsification surgical handpieces commercialized by Alcon, Inc. For instance, FIG. 7 illustrates conventional tips 100 with a single, attached sleeve 102 and FIG. 8 illustrates such a surgical handpiece 110 attached to the tip with the single, attached sleeve. The tips and surgical handpiece of FIGS. 7 and 8 are available from Alcon, Inc.

As best understood from FIG. 7, the single sleeve goes over the phacoemulsification needle—irrigation fluid flows in the space between the exterior of the phacoemulsification needle and the interior of the sleeve. The phacoemulsification needle extends from an opening in the distal end of the sleeve. There are one or two ports 104 in the sleeve wall near the distal end through which irrigation fluid flows into the eye. As shown in FIG. 8, the proximal end of the sleeve is coupled to the phacoemulsification surgical hand piece (via a threaded connection 106—though the sleeve can be pushed over the threads on the hand piece).

The distal end of the single sleeve is open so that the needle can pass through the single sleeve. The threaded connection is meant to fluidly seal to the phacoemulsification surgical hand piece so that irrigation fluid can flow through the hand piece, through the sleeve, and into the eye. Irrigation fluid flows through the top connector 112 in FIG. 8, through the tube 108 on top of the hand piece 110, and into the irrigation sleeve 102, which surrounds the phacoemulsificaion needle. The sleeve is made of a flexible silicone. There are no protuberances on the phacoemulsification needle—it is smooth and cylindrical, often bent at an angle.

By adding multiple sleeves in accordance with the embodiments of FIGS. 1-6 of the present application to the conventional tip of FIG. 7, the surgical handpiece of FIG. 8 could deliver fluid to the multiple sleeves in a manner analogous to its delivery of irrigation fluid via the top connector and tube on top of the handpiece in FIG. 8. As shown in FIG. 6, perforating the middle sleeve 90 enables the irrigation fluid to pass from the middle passage 95 between the inner and middle sleeves 20. 90 to reach the outer passage 15 between the middle and outer sleeves 90, 10. Further, if the fluid is delivered to the inner passage 25, then the inner sleeve 20 may be perforated to help in passage of fluid to the middle and outer passages 95, 15.

Alcon, Inc. commercializes phacoemulsification tips whose inner sleeve is free floating. When their inner sleeve is placed on tips with an angulated distal portion of the tip (approximately 5 mm in length), the angulation prevents them from slipping off the end. On straight tips, either the tip of the needle (again approximately 5 mm) has a larger outer diameter (called the "flared" tip) or protuberances on the needle (such as 5 mm from the tip) have been used to prevent forward migration.

Figure 9:
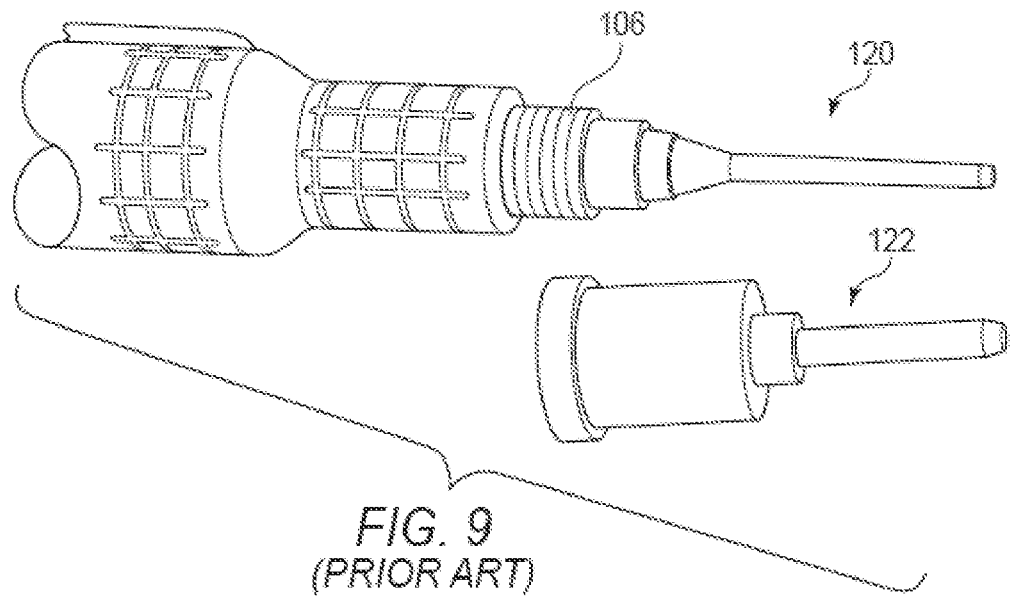
FIG. 9 is a top view of a further conventional phacoemulsification needle and sleeve to be placed over the needle.
Figure 10:
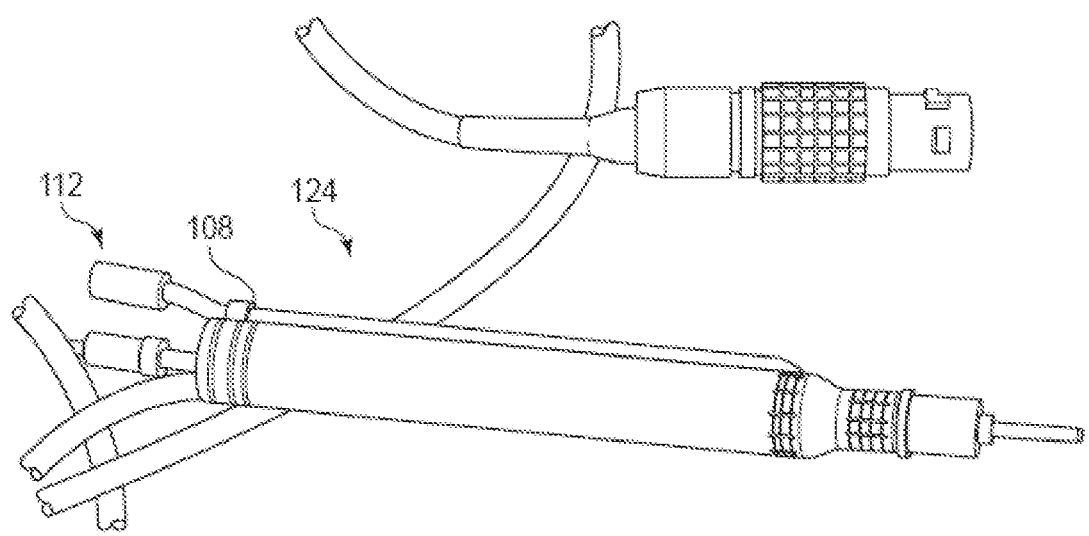
FIG. 10 is a top view of a further conventional an ultrasonic, vibrating, phacoemulsification surgical handpiece with the needle of FIG. 9 over which is placed the sleeve of FIG. 9.

FIGS. 9 and 10 show a further conventional phacoemulsification handpiece 124 with needle 120 and sleeve 122. The sleeve 122 of FIG. 9 is incompressible and fitted over the needle 120 of FIG. 9 and is sealed to threads 106 of the tip to realize a sleeved needle as in FIG. 10. As in FIG. 7, irrigation fluid enters through a threaded connector 112 to pass through a tube 108 to deliver fluid to the tip at a location between the sleeve 122 and the needle 120 to enable emulsification of the nucleus of the eye. Fluid that flows between the sleeve and the needle acts as a coolant and avoids burning of the cornea by the vibrating needle. FIGS. 9 and 10 are from the webpage: http://www.mrcophth.com/ophthalmicinstruments/cataractextraction/phacoinstruments.html.

With respect to all the embodiments, the inner rigid sleeve 20 may or may not be present and may or may not be free floating. Further, the middle sleeve 90 may or may not be present. In addition, the outer sleeve 10 should always be present and may or may not have a scalloped end. The inner rigid sleeve 20 and the middle sleeve 90, if present, enter the eye, but the outer sleeve 10 does not enter the eye.

Therefore, there may be all 3 sleeves present, i.e., inner rigid sleeve 20 that enters the eye and may or may not be free floating, the middle sleeve 90 that enters the eye and the outer sleeve 10 that does not enter the eye. Alternatively, there may be only two of the three sleeves present. For instance, there may be present just the inner rigid sleeve 20 that may or may not be free floating and the outer sleeve 10. Otherwise, there may be no inner rigid sleeve 20 present but the other two sleeves 10, 90 may be present. Finally, there may be only one of the three sleeves present, i.e., the outermost sleeve 10 that does not enter the eye yet abuts the ocular tissue at the incision on the exterior surface of the eye.

While the foregoing description and drawings represent the preferred embodiment of the present invention, it will be understood that various changes and modifications may be made without departing from the scope of the present invention.

What is claimed is:

1. A multi-sleeved surgical vibrating tool suited for performing phacoemulsification through an incision and for preventing thermal injury otherwise caused by friction and heat generation from the tool, comprising:

a surgical handpiece of the multi-sleeved surgical vibrating tool, the surgical handpiece being configured to perform phacoemulsification, the surgical handpiece including a hollow, vibratory needle that includes a shaft that terminates distally into a ported tip, and a driver that drives the vibratory needle to effect oscillatory vibratory motion; and a plurality of concentric sleeves each of different diameter from each other and also concentric with the shaft of the hollow, vibratory needle, the plurality of concentric sleeves including an inner sleeve and an outer sleeve, the outer sleeve being configured to guide fluid to exit the outer sleeve to prevent thermal injury to tissue otherwise caused by friction and heat generation from driving of the vibratory needle, a distal end of the inner sleeve being arranged to protrude longitudinally further than a distal end of the outer sleeve so as to be closer longitudinally to a distal end of the needle than is the distal end of the outer sleeve as the fluid exits the outer sleeve, the distal end of the outer sleeve defining a pattern of peak and valley formations that permit the fluid to exit the outer sleeve via the valley formations.

2. The tool of claim 1, wherein the concentric sleeves include a middle sleeve located spatially between the inner sleeve and the outer sleeve, the needle and the inner sleeve being spaced apart from each other to define therebetween an inner passage, the inner and middle sleeves being spaced apart from each other to define therebetween a middle passage, the middle and outer sleeves being spaced apart from each other to define therebetween an outer passage, the surgical handpiece being configured to deliver fluid to at least one of the middle and outer passages to allow the outer passage to guide the fluid to exit the outermost sleeve to cool the tissue.

3. The tool of claim 2, wherein the distal end of the outer sleeve has the peak and valley formations arranged so that the peak formations are further from a proximal end of the outer sleeve than are the valley formations to allow just the peak formations to abut the tissue, the outer sleeve being configured to guide the fluid to flow through the outer passage to exit by passing across the valley formations to reach the tissue and thereby prevent the thermal injury.

4. The tool of claim 1, wherein the outer sleeve is compressible in a direction of elongation of the outer sleeve.

5. The tool of claim 2, wherein at least one of the middle and outer sleeves are configured to change a direction of fluid flow through the outer passage in a region within confines of the at least one of the middle and outer sleeves at a region that neighbors the distal end of the at least one of the middle and outer sleeves.

6. The tool of claim 1, wherein the distal end of the outer sleeve is serrated or scalloped to define the peak and valley formations.

7. A multi-sleeved surgical vibrating tool suited for performing phacoemulsification through an incision and for preventing thermal injury otherwise caused by friction and heat generation from the tool, comprising:
a surgical handpiece of the multi-sleeved surgical vibrating tool, the surgical handpiece being configured to perform phacoemulsification, the surgical handpiece including a hollow, vibratory needle that includes a shaft that terminates distally into a ported tip, and a driver that drives the vibratory needle to effect oscillatory vibratory motion; and
a plurality of concentric sleeves each of different diameter from each other and also concentric with the shaft of the hollow, vibratory needle, the plurality of concentric sleeves including an inner sleeve and an outer sleeve, the outer sleeve being configured to guide fluid to exit the outer sleeve to prevent thermal injury to tissue otherwise caused by friction and heat generation from driving of the vibratory needle, a distal end of the inner sleeve being arranged to protrude longitudinally further than a distal end of the outer sleeve so as to be closer longitudinally to a distal end of the needle than is the distal end of the outer sleeve as the fluid exits the outer sleeve, the concentric sleeves include a middle sleeve located spatially between the inner sleeve and the outer sleeve, the needle and the inner sleeve being spaced apart from each other to define therebetween an inner passage, the inner and middle sleeves being spaced apart from each other to define therebetween a middle passage, the middle and outer sleeves being spaced apart from each other to define therebetween an outer passage, the surgical handpiece being configured to deliver fluid to at least one of the middle and outer passages to allow the outer passage to guide the fluid to exit the outermost sleeve to cool the tissue the middle sleeve being more flexible and compressible than the inner sleeve.

8. The tool of claim 1, wherein the inner sleeve is unattached and free to float about the needle.

9. The tool of claim 2, wherein the middle sleeve is perforated to permit fluid flow through perforations in the middle sleeve to enter the outer passage.

10. The tool of claim 2, wherein proximal ends of the middle and outer sleeves are sealed in a liquid-tight manner.

11. The tool of claim 2, wherein a distal end of the middle sleeve is arranged to protrude longitudinally further than the distal end of the outer sleeve so as to be closer longitudinally to the distal end of the needle than is the distal end of the outer sleeve as the fluid exits the outer sleeve.

12. The tool of claim 1, wherein the distal end of the outer sleeve is configured to abut tissue, the outer sleeve having recesses neighboring the distal end of the outer sleeve that are closer to the distal end of the outer sleeve than to a proximal end of the outer sleeve, the recesses being arranged so that the fluid exits via the recesses to drain along an exterior facing surface of the outer sleeve to cool the tissue that the distal end of the outer sleeve abuts.

13. A method of performing phacoemulsification through an incision and preventing thermal injury otherwise caused by friction and heat generation from a multi-sleeved surgical tool, comprising the steps of:
driving a hollow, vibratory needle of a surgical handpiece to effect oscillatory vibratory motion, the hollow, vibratory needle having a shaft that terminates distally into a ported tip, and
guiding fluid with a plurality of concentric sleeves, the concentric sleeves including an outer sleeve and an inner sleeve, the guiding including guiding the fluid with the outer sleeve to exit to effect cooling to prevent thermal injury to tissue otherwise caused by friction and heat generation from the driving of the hollow, vibratory needle, the concentric sleeves each being of a different diameter from each other and also being concentric with the shaft of the needle, a distal end of the inner sleeve being arranged to protrude longitudinally further than a distal end of the outer sleeve so that the distal end of the inner sleeve is closer longitudinally to a distal end of the needle than is the distal end of the outer sleeve as the fluid exits the outer sleeve, the distal end of the outer sleeve defining a pattern of peak and valley formations that permit the fluid to exit the outer sleeve via the valley formations.

14. The method of claim 13, wherein the concentric sleeves include a middle sleeve located spatially between the inner sleeve and the outer sleeve, the needle and the inner sleeve being spaced apart from each other to define therebetween an inner passage, the inner and middle sleeves being spaced apart from each other to define therebetween a middle passage, the middle and outer sleeves being spaced apart from each other to define therebetween an outer passage, and delivering the fluid to at least one of the middle and outer passages to allow the guiding of the fluid by the outer sleeve to flow past the distal end of the outer sleeve.

15. The method of claim 14, wherein the distal end of the outer sleeve has the peak and valley formations arranged so that the peak formations are further from a proximal end of the outer sleeve than are the valley formations so just the peak formations abut the tissue, the outer sleeve being configured to guide the fluid to flow through the outer passage to reach the tissue and to exit by passing across the valley formations to thereby prevent the thermal injury.

16. The method of claim 14, further comprising freely floating the inner sleeve and keeping the inner sleeve unattached, the middle sleeve and the outer sleeve each having a proximal end that is sealed in a liquid-tight manner.

17. The method of claim 14, wherein the guiding includes flowing the fluid through perforations in the middle sleeve.

18. The method of claim 14, further comprising changing a direction of flow of the fluid through at least one of the middle and outer passages in a region within confines of the at least one of the middle and outer passages at a region neighboring a distal end of at least one of the middle and outer sleeves.

19. A multi-sleeved surgical vibrating tool suited for performing phacoemulsification through an incision and for preventing thermal injury otherwise caused by friction and heat generation from the tool, comprising:
 a surgical handpiece of the multi-sleeved surgical vibrating tool, the surgical handpiece being configured to perform phacoemulsification, the surgical handpiece including a hollow, vibratory needle that includes a shaft that terminates distally into a ported tip, and a driver that drives the vibratory needle to effect oscillatory vibratory motion;
 a plurality of concentric sleeves each of different diameter from each other and also concentric with the shaft of the hollow, vibratory needle, the plurality of concentric sleeves including an inner sleeve and an outer sleeve, the outer sleeve being configured to guide fluid to exit the outer sleeve to prevent thermal injury to tissue otherwise caused by friction and heat generation from driving of the vibratory needle, a distal end of the inner sleeve being arranged to protrude longitudinally further than a distal end of the outer sleeve so as to be closer longitudinally to a distal end of the needle than is the distal end of the outer sleeve as the fluid exits the outer sleeve; and
 compressing the outer sleeve in a direction of elongation of the outer sleeve.

20. The method of claim 14, wherein a distal end of the middle sleeve protrudes longitudinally further than the distal end of the outer sleeve so as to be closer longitudinally to the distal end of the needle than is the distal end of the outer sleeve as the fluid exits the outer sleeve.

21. The method of claim 14, wherein the distal end of the outer sleeve abuts the tissue, the outer sleeve having recesses neighboring the distal end of the outer sleeve that are closer to the distal end of the outer sleeve than to a proximal end of the outer sleeve, the recesses being arranged so that the fluid exits via the recesses to drain along an exterior facing surface of the outer sleeve to cool the tissue that the distal end of the outer sleeve abuts.

22. The method of claim 13, further comprising serrating or scalloping the distal end of the outer sleeve to form the peak and valley formations.

23. A method of performing phacoemulsification through an incision and preventing thermal injury otherwise caused by friction and heat generation from a multi-sleeved surgical tool, comprising the steps of:
 driving a hollow, vibratory needle of a surgical handpiece to effect oscillatory vibratory motion, the hollow, vibratory needle having a shaft that terminates distally into a ported tip, and
 guiding fluid with a plurality of concentric sleeves, the concentric sleeves including an outer sleeve and an inner sleeve, the guiding including guiding the fluid with the outer sleeve to exit to effect cooling to prevent thermal injury to tissue otherwise caused by friction and heat generation from the driving of the hollow, vibratory needle, the concentric sleeves each being of a different diameter from each other and also being concentric with the shaft of the needle, a distal end of the inner sleeve being arranged to protrude longitudinally further than a distal end of the outer sleeve so that the distal end of the inner sleeve is closer longitudinally to a distal end of the needle than is the distal end of the outer sleeve as the fluid exits the outer sleeve, the concentric sleeves include a middle sleeve located spatially between the inner sleeve and the outer sleeve, the needle and the inner sleeve being spaced apart from each other to define therebetween an inner passage, the inner and middle sleeves being spaced apart from each other to define therebetween a middle passage, the middle and outer sleeves being spaced apart from each other to define therebetween an outer passage, and delivering the fluid to at least one of the middle and outer passages to allow the guiding of the fluid by the outer sleeve to flow past the distal end of the outer sleeve, the middle sleeve being more flexible and compressible than the inner sleeve.

* * * * *